(12) United States Patent
Kruse et al.

(10) Patent No.: US 11,311,284 B2
(45) Date of Patent: Apr. 26, 2022

(54) SUTURE TENSIONING AND SECUREMENT DEVICE, SYSTEM, AND METHODS

(71) Applicant: Speed Clip Solutions, LLC, Dallas, TX (US)

(72) Inventors: Kevin Kruse, Dallas, TX (US); Lawrence Binder, Miami, FL (US)

(73) Assignee: Speed Clip Solutions, LLC, Dallas, TX (US)

( * ) Notice: Subject to any disclaimer, the term of this patent is extended or adjusted under 35 U.S.C. 154(b) by 245 days.

(21) Appl. No.: 16/811,923

(22) Filed: Mar. 6, 2020

(65) Prior Publication Data
US 2020/0281580 A1     Sep. 10, 2020

Related U.S. Application Data

(60) Provisional application No. 62/863,383, filed on Jun. 19, 2019, provisional application No. 62/816,633, (Continued)

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0496* (2013.01)

(58) Field of Classification Search
CPC .......... A61B 17/06166; A61B 17/0401; A61B 17/0487; A61B 2017/0496;
(Continued)

(56) References Cited

U.S. PATENT DOCUMENTS

| 5,282,832 A | 2/1994 | Toso et al. |
| 5,702,397 A | 12/1997 | Marlowe et al. |

(Continued)

FOREIGN PATENT DOCUMENTS

| EP | 2429409 | 3/2012 |
| WO | 0197677 A2 | 12/2001 |

(Continued)

OTHER PUBLICATIONS

PCT Notification of Transmittal of the International Search Report and the Written Opinion of the International Searching Authority, issued to Application No. PCT/US2020/021500, dated Jun. 19, 2020.

*Primary Examiner* — Phong Son H Dang
(74) *Attorney, Agent, or Firm* — Heslin Rothenberg Farley & Mesiti PC

(57) ABSTRACT

A system and methods for gathering, tensioning, and clamping a plurality of suture leads may be used for any of a range of possible surgical applications. The system includes a suture clamp assembly that includes receptacle and plug components, wherein suture leads passed into the receptacle are secured when the plug is inserted into the receptacle to lock the suture leads in place, a gathering suture that includes a gathering loop, an instrument for securement of the plurality of suture leads, and optionally an anchor affixed to the gathering suture. The system may be used to address rotator cuff repairs, labral repair, biceps tenodesis, acromioclavicular joint stabilization, and applications in other joints and bones within a body.

14 Claims, 14 Drawing Sheets

Related U.S. Application Data filed on Mar. 11, 2019, provisional application No. 62/814,700, filed on Mar. 6, 2019.

(58) Field of Classification Search
CPC ...... A61B 2017/044; A61B 2017/0409; A61B 2017/0417; A61B 2017/0488; A61F 2/0811

See application file for complete search history.

(56) References Cited

U.S. PATENT DOCUMENTS

| | | | | |
|---|---|---|---|---|
| 5,993,451 | A | 11/1999 | Burkhart | |
| 6,086,608 | A * | 7/2000 | Ek | A61B 17/0487 606/232 |
| 6,200,329 | B1 | 3/2001 | Fung et al. | |
| 6,214,031 | B1 | 4/2001 | Schmieding et al. | |
| 6,475,230 | B1 * | 11/2002 | Bonutti | A61B 17/0487 606/232 |
| 6,511,499 | B2 | 1/2003 | Schmieding et al. | |
| 6,527,794 | B1 * | 3/2003 | McDevitt | A61B 17/0401 606/1 |
| 6,544,281 | B2 | 4/2003 | El Attrache et al. | |
| 6,629,977 | B1 | 10/2003 | Wolf | |
| 6,656,185 | B2 | 12/2003 | Gleason et al. | |
| 6,660,023 | B2 | 12/2003 | McDevitt et al. | |
| 6,857,216 | B1 | 2/2005 | Merin | |
| 7,081,126 | B2 | 7/2006 | McDevitt et al. | |
| 7,083,638 | B2 | 8/2006 | Foerster | |
| 7,090,690 | B2 | 8/2006 | Foerster et al. | |
| 7,195,634 | B2 | 3/2007 | Schmieding et al. | |
| 7,303,568 | B2 | 12/2007 | Jannot | |
| 7,322,986 | B2 | 1/2008 | Wolf | |
| 7,329,272 | B2 | 2/2008 | Burkhart et al. | |
| 7,749,236 | B2 * | 7/2010 | Oberlaender | A61B 17/0483 606/148 |
| 7,993,369 | B2 | 8/2011 | Dreyfuss | |
| 8,202,295 | B2 | 6/2012 | Kaplan | |
| 8,343,186 | B2 | 1/2013 | Dreyfuss et al. | |
| 8,382,776 | B2 | 2/2013 | Ducharme | |
| 8,430,909 | B2 | 4/2013 | Dreyfuss | |
| 8,444,674 | B2 | 5/2013 | Kaplan | |
| 8,545,536 | B2 | 10/2013 | Mayer et al. | |
| 8,623,052 | B2 | 1/2014 | Dreyfuss et al. | |
| 8,663,280 | B2 | 3/2014 | Kaplan | |
| 8,801,755 | B2 | 8/2014 | Dreyfuss et al. | |
| 8,821,541 | B2 | 9/2014 | Dreyfuss et al. | |
| 9,034,014 | B2 | 5/2015 | Catania et al. | |
| 9,179,907 | B2 | 11/2015 | El Attrache et al. | |
| 9,226,817 | B2 | 1/2016 | Dougherty et al. | |
| 9,386,976 | B2 | 7/2016 | Mayer et al. | |
| 9,414,834 | B2 | 8/2016 | Palese | |
| 9,510,816 | B2 | 12/2016 | McDevitt et al. | |
| 9,566,060 | B2 | 2/2017 | Dougherty et al. | |
| 9,706,986 | B2 | 7/2017 | El Attrache et al. | |
| 9,757,112 | B2 | 9/2017 | Kaplan | |
| 9,770,240 | B2 | 9/2017 | Dougherty et al. | |
| 9,775,599 | B2 | 10/2017 | El Attrache et al. | |
| 9,782,250 | B2 | 10/2017 | Dougherty et al. | |
| 9,788,825 | B2 * | 10/2017 | Whittaker | A61B 17/0469 |
| 9,855,132 | B2 | 1/2018 | Hoover et al. | |
| 9,907,548 | B2 | 3/2018 | Dougherty et al. | |
| 10,052,091 | B2 | 8/2018 | Dreyfuss et al. | |
| 10,076,377 | B2 * | 9/2018 | Bonutti | A61B 17/12131 |
| 10,149,752 | B2 | 12/2018 | Dougherty et al. | |
| 10,201,344 | B2 | 2/2019 | Palese | |
| 10,390,817 | B2 * | 8/2019 | Bonutti | A61B 17/8869 |
| 10,426,459 | B2 | 10/2019 | Fallin et al. | |
| 10,492,901 | B2 | 12/2019 | Hoover et al. | |
| 2005/0277986 | A1 | 12/2005 | Foerster et al. | |
| 2006/0271060 | A1 * | 11/2006 | Gordon | A61B 17/0401 606/103 |
| 2006/0271105 | A1 | 11/2006 | Foerster et al. | |
| 2008/0033460 | A1 * | 2/2008 | Ziniti | A61B 17/0487 606/148 |
| 2008/0077161 | A1 | 3/2008 | Kaplan | |
| 2009/0099598 | A1 | 4/2009 | McDevitt et al. | |
| 2009/0292321 | A1 | 11/2009 | Collette | |
| 2009/0326562 | A1 * | 12/2009 | White | A61B 17/06166 606/148 |
| 2010/0087857 | A1 * | 4/2010 | Stone | A61B 17/0401 606/232 |
| 2010/0106194 | A1 * | 4/2010 | Bonutti | A61B 17/0482 606/279 |
| 2011/0009884 | A1 | 1/2011 | Kaplan | |
| 2012/0123447 | A1 * | 5/2012 | Corrao | A61B 17/04 606/144 |
| 2013/0144335 | A1 | 6/2013 | Sandrow | |
| 2014/0180313 | A1 * | 6/2014 | Harrison | A61B 17/0482 606/145 |
| 2015/0073440 | A1 | 3/2015 | Li | |
| 2015/0289866 | A1 | 10/2015 | Bowen | |
| 2016/0015378 | A1 | 1/2016 | Zirps et al. | |
| 2016/0228117 | A1 | 8/2016 | Borden | |
| 2016/0310127 | A1 | 10/2016 | Cavallazzi et al. | |
| 2017/0065274 | A1 | 3/2017 | Mayer et al. | |
| 2017/0303912 | A1 | 10/2017 | El Attrache et al. | |
| 2017/0333028 | A1 | 11/2017 | Kaplan | |
| 2018/0008255 | A1 | 1/2018 | Fallin et al. | |
| 2018/0235598 | A1 | 8/2018 | Burkhart et al. | |
| 2018/0235599 | A1 | 8/2018 | Burkhart et al. | |
| 2019/0282285 | A1 | 9/2019 | Bonutti et al. | |
| 2019/0290420 | A1 | 9/2019 | Dougherty et al. | |
| 2019/0380696 | A1 | 12/2019 | Taber et al. | |

FOREIGN PATENT DOCUMENTS

| | | |
|---|---|---|
| WO | 0197677 A3 | 4/2002 |
| WO | 0238059 S2 | 5/2002 |
| WO | 0238059 A3 | 2/2003 |
| WO | 2004045367 S2 | 6/2004 |
| WO | 2004045367 A3 | 4/2005 |
| WO | 2007109769 | 9/2007 |
| WO | 2007147634 A1 | 12/2007 |
| WO | 2008011417 A3 | 11/2008 |
| WO | 2009146155 A1 | 12/2009 |
| WO | 2010115113 A1 | 10/2010 |
| WO | 2011097672 A1 | 8/2011 |
| WO | 2012037700 A1 | 3/2012 |
| WO | 2012100359 A1 | 8/2012 |
| WO | 2013091194 A1 | 6/2013 |
| WO | 201410767 A1 | 7/2014 |
| WO | 2014183826 A1 | 11/2014 |
| WO | 2015157663 A1 | 10/2015 |
| WO | 2016123199 A1 | 8/2016 |
| WO | 2016141072 A2 | 9/2016 |
| WO | 2016141072 A3 | 11/2016 |
| WO | 2018048863 A1 | 3/2018 |
| WO | 2019108222 A1 | 6/2019 |
| WO | 2019108224 A1 | 6/2019 |

* cited by examiner

SUTURE TENSIONING AND SECUREMENT DEVICE, SYSTEM, AND METHODS

PRIORITY

The present application claims priority to and the claims the benefit of U.S. Provisional Patent Application Ser. No. 62/814,700, filed Mar. 6, 2019, 62/816,633, filed Mar. 11, 2019, and 62/863,383, filed Jun. 19, 2019, each with the title "SUTURE LOCK AND TENSION INSTRUMENT," each of which is hereby incorporated by reference in its entirety.

FIELD OF THE INVENTION

Provided herein are suture tensioning and securement devices, system, and methods for securing two or more suture leads. The benefits realized include the ability to secure multiple suture leads to a single fixation point while minimizing or eliminating reliance on knotting any one or more of the suture leads.

BACKGROUND OF THE INVENTION

In the field of rotator cuff repair surgery transosseous fixation is considered the gold standard because it is shown to provide good and even excellent long-term outcomes for the patient and is demonstrated to provide suitable performance based on biomechanical studies. Using modern arthroscopic techniques, excellent fixation strength and excellent outcomes are possible if executed by an experienced arthroscopic surgeon. And arthroscopic rotator cuff repair provides advantages over open repair, including visual access to the glenohumeral joint to evaluate pathology and characterize tear patterns, preservation of the deltoid origin, and a reduced incidence of reports of postoperative pain and stiffness.

A variety of fixation techniques and configurations are used in arthroscopic rotator cuff repair that employ multiple sutures, each suture passed through the tissue to be repaired, where each suture typically includes two loose ends or "leads," or in some examples includes one lead and one secured end that is affixed to an anchor secured in bone. Securement of these suture loose ends or leads is necessary to maintain tension on each suture to secure and repair the tissue, hence the leads must be secured by means that can include knotting, and suture anchors. For most surgeons, suture anchors are the primary means of fixation of suture leads. A suture anchor is a metal, plastic or textile device that is typically driven and/or actuated for securement by toggle, knotting or friction fixation within bone, wherein toggle and knotting fixation typically involves securement against an inner surface of cortical bone adjacent cancellous bone. Currently suture leads are attached to bone anchors or tied in knots with adjacent suture leads.

Depending on the configuration of suture placement, a surgeon may have a large number of suture leads to secure once the tissue has been sutured. For example, one known surgical technique involves double-row transosseous fixation, which has been shown to be a superior method of rotator cuff repair fixation, with improved biomechanical characteristics (i.e., strength, stiffness, load to failure, and gapping), increased compression across the rotator cuff footprint for maximal healing, and high radiographic healing rates. Despite these benefits, there are inefficiencies in the surgical suite in terms of substantially increased surgical time and implant cost by virtue of use of what may be twice as many suture anchors. In addition, there may be unacceptable compromise to bone when multiple anchors are secured within the bone, for example in the tuberosity footprint, and/or there is poor bone stock to support anchor fixation.

Furthermore, where knotting of suture leads is employed to achieve fixation, there are inefficiencies in the surgical suite in terms of substantially increased surgical time due to the challenges of tying knots in many leads, and associated challenges which include lead breakage, and cuts to the surgeon's gloves and/or fingers. Learning to tie suture leads requires extensive training for surgeons. Tying multiple suture leads in the operating room requires significant time and can lead to unsecured suture leads. There are several examples in the art of clips and special type suture materials that help address some of the challenges associated with the use of anchors and knots in suture leads. But such devices used in the art are generally focused on soft tissue and low force suture applications. For rotator cuff surgery, secured sutures are typically exposed to significant force equal to that applied to a suture knot. And many of the clip designs in the art apply sharp point loads to the suture material causing potential failure points in the suture lead.

The challenges are many for surgical procedures that involve securing soft tissue to bone, for example, in the context of a rotator cuff repair. Accordingly, improvements in devices, systems, and methods are needed to ensure the positive outcomes and minimize challenges and risks.

SUMMARY OF THE INVENTION

The present invention provides alternate embodiments of a suture clamp assembly that includes receptacle and plug components, wherein the receptacle component incorporates rounded lead in and lead out features that contact with suture leads passed into the receptacle and serve to minimize deformation of the suture leads when the plug is inserted into the receptacle to lock the suture leads in place. The present invention further provides an instrument for securement of a plurality of suture leads by employing the suture clamp assembly, a gathering suture that includes a gathering loop, and optionally an anchor affixed to the gathering suture. Typically, suture leads are knotted individually. The present invention allows for the gathering, pre-tensioning, final tensioning, and clamping of one or a plurality of suture leads. In some examples from at least one to twenty suture leads or more may be utilized. The suture gathering loop of the gathering suture, the suture clamp assembly and the securement instrument may be used for any of a range of possible surgical applications, including but not limited to, surgery to address rotator cuff repairs, as exemplified herein. Other examples include labral repair, biceps tenodesis, acromioclavicular joint stabilization, and applications in other joints within a body.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

REFERENCE NUMBERS USED IN THE SPECIFICATION AND DRAWINGS

Figure 1:
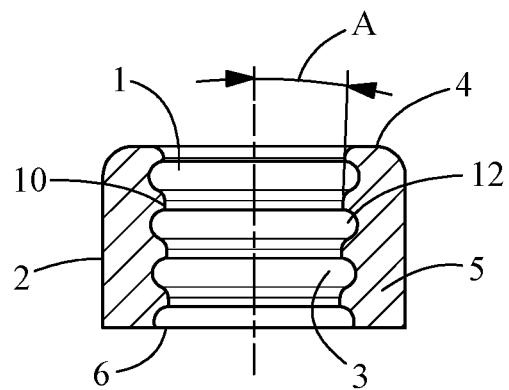
FIG. 1 shows a base receptacle of a clamp assembly according to the disclosure, the base receptacle having a tapered ribbed interior surface.

The following table provides a key to the specific features mentioned in the specification which are numbered in the text or otherwise correspond to the indicated numbers in the table

| Feature | REF # |
| --- | --- |
| Suture Clamp assembly | 9 |
| Base receptacle | 5 |
| Through channel | 1 |
| Exterior surface | 2 |
| Receiver seat | 3 |
| Upper end | 4 |
| Lower end | 6 |
| Interior surface | 10 |
| Receiver engagement feature | 12 |
| Plug | 7 |
| Proximal end | 11 |
| Distal end | 13 |
| Exterior surface (ribbed) | 14 |
| Plug engagement feature | 16 |
| Driving feature | 40 |
| Suture | 18 |
| Suture lead | 19 |
| Secured end | 17 |
| Securement instrument | 21 |
| Handle | 20 |
| Trigger | 22 |
| Carriage assembly | 23 |
| Upper slide | 24 |
| Plug inserter | 26 |
| Tension ring (lead clamp) | 28 |
| Suture slots | 29 |
| Pinion knob | 30 |
| Tension dial | 32 |
| Mounting tip | 34 |
| Rack | 36 |
| Ratchet | 38 |
| Gathering suture | 41 |
| Gathering suture lead | 42 |
| Anchor engagement portion | 43 |
| Lasso portion | 44 |
| Knot | 45 |
| Eyelet | 50 |
| Eyelet aperture | 51 |
| Eyelet portion | 52 |
| Gathering loop | 53 |
| Loop portion | 54 |
| One-way mechanism | 60 |
| Bone (humerus) | 70 |
| Bone hole | 72 |
| Tunnel | 75 |
| Anchor securement hole | 76 |
| Anchor | 100 |
| Suture lead locking | 80 |
| Cancellous bone | 81 |
| Cortical bone | 82 |

-continued

| Feature | REF # |
| --- | --- |
| Bone outer surface | 84 |
| Cortical bone under surface | 86 |
| Generic suture clamp | 90 |
| Steps 201-210 of a method | 200 |

Features and advantages of the general inventive concepts will become apparent from the following description made with reference to the accompanying drawings, including drawings represented herein in the attached set of figures, of which the following is a brief description:

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

This description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care. More broadly, in connection with non-medical uses of the inventions described herein, the term refers to a user of one or more components of the suture clamp assembly 9.

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The term "proximal" as used in connection with any object refers to the portion of the object that is closest to the operator of the object (or some other stated reference point), and the term "distal" refers to the portion of the object that is farthest from the operator of the object (or some other stated reference point). A "clinical subject" refers to a human or other animal who is the subject of treatment with a bone fixation or reduction device in accordance with the disclosure. With respect to any references herein that may be made relative to a clinical subject, the term "medial" indicates a direction toward the centerline axis (e.g. the spine) of the clinical subject, and the term "lateral" indicates a direction toward a side of the clinical subject. As used herein in the described and illustrated embodiments, the term "device" means and refers to any one of a suture, a suture clamp assembly 9 assembly or one or more of its parts (a suture clamp assembly 9 may sometimes referred to in the art as a clip), a securement instrument, an anchor, and a suture. The term "system" refers to any combination of two or more of devices. The term "lead" as used specifically herein pertains to a free end of a suture. And the term "method" refers to any one of methods of using a device or system, and surgical methods or techniques employing a device or system.

Figure 5:
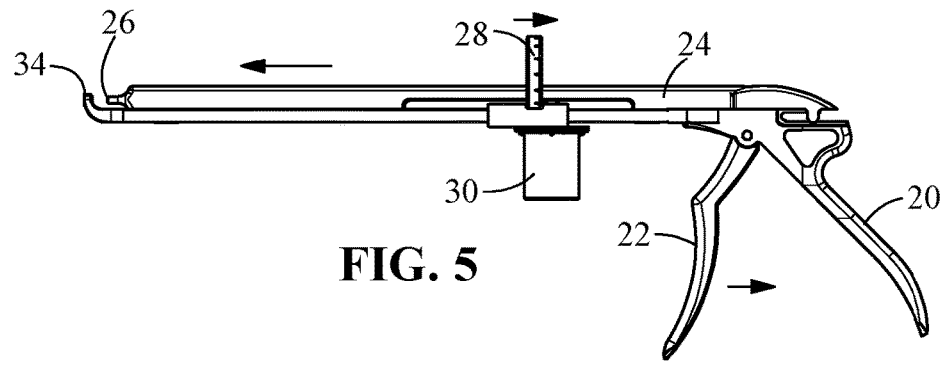
FIG. 5 shows a tensioner instrument from a side profile view.
Figure 6:
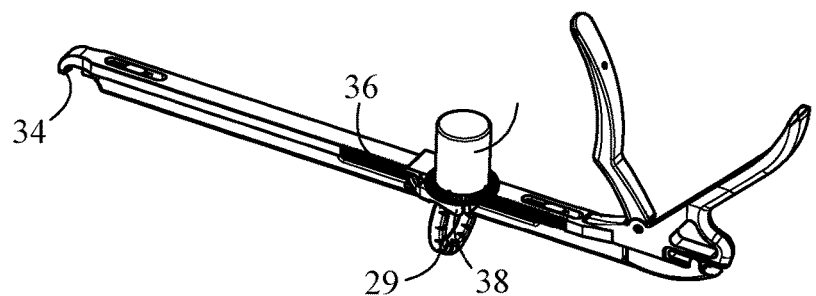
FIG. 6 shows a tensioner instrument from an oblique bottom view (opposite side)
Figure 7:
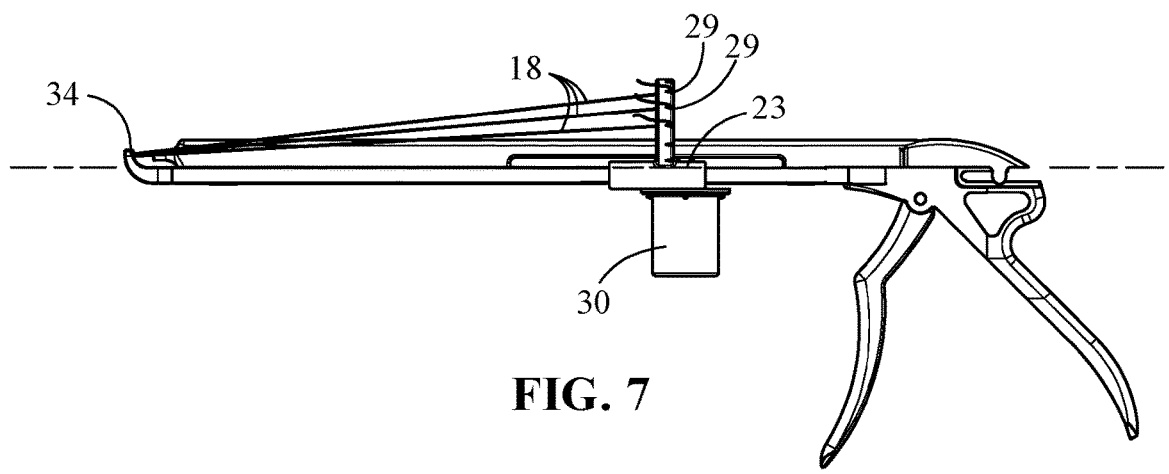
FIG. 7 shows a tensioner instrument from a side profile view with suture leads attached to the carriage.

Referring now to the drawings, the present invention includes a suture clamp assembly 9 that holds one or more suture leads securely. FIGS. 1-3 and FIGS. 8-10 show two alternate embodiments of the suture clamp assembly 9. FIGS. 5-7 show alternative views of a securement instrument 30 that provides tensioning and locking capabilities. FIGS. 12-16 show an arrangement of suture leads 18, including a one-way device 60 and a gathering loop 53 that illustrate a method for gathering and tensioning suture leads 18 prior to placement of the suture clamp assembly 9. And FIGS. 17-29 further illustrate a method for gathering, tensioning and securing suture leads in the context of representative anatomy, namely the shoulder joint, which is relevant in connection with rotator cuff surgery. It will be appreciated by one of skill in the art that the devices, system, and methods according to the disclosure are suitable for other anatomical sites in the body wherein one or a plurality of suture leads may be tensioned for securement of soft tissue relative to bone. Thus, the invention is not limited to use for rotator cuff type repairs of the shoulder and may be employed at any other anatomical site.

Figure 3:
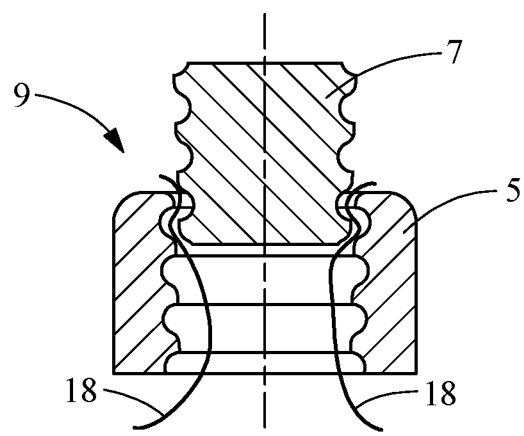
FIG. 3 shows an assembly of the base receptacle and the plug.
Figure 4:
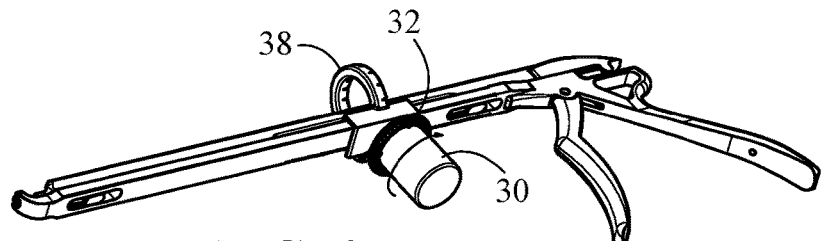
FIG. 4 shows a tensioner instrument from an oblique bottom view.

Referring again to the drawings FIG. 3 shows a first embodiment of a component of a clamp assembly according to that includes a base receptacle 5 and a plug 7. In some embodiments the suture clamp assembly 9 is pre-assembled or manufactured and assembled as one piece, wherein in use the plug 7 is insertable into a through channel 1 of the base receptacle 5. In other embodiments, the suture clamp assembly 9 is provided in an unassembled state. Referring now to FIG. 4, a securement instrument 30 is shown which is adapted with a distal mounting tip 34 to receive and retain a base receptacle of a suture clamp assembly 9 to enable passage of one or more sutures through the through channel 1.

In the various embodiments, the complimentary mating surfaces comprising the receiver and plug engagement features 12, 16 of the clamp 9 components may be selected from a series of circumferential grooves on the receptacle 5 and ribs on the plug 7, or spiral grooves on the receptacle and threads on the plug 7. Of course, other configurations are possible. In the various embodiments, the components inter-engage by snap fitting or threaded engagement between the complimentary surfaces. The complimentary surfaces generally lack sharp edges and angles to prevent cutting the sutures passed therethrough and are adapted with sufficient clearance to prevent binding and shearing of the sutures.

Figure 2:
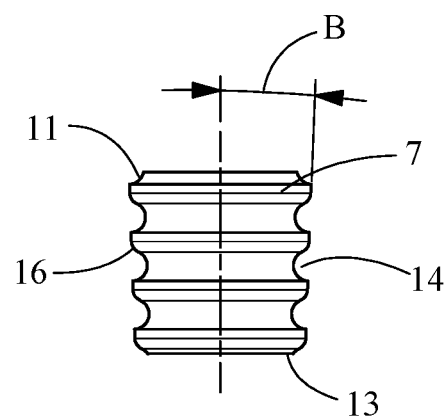
FIG. 2 shows a plug with a tapered ribbed interior surface.

Referring now to FIG. 2, in an embodiment of the present invention, a base receptacle 5, and plug 7, is provided to hold one or more suture leads 18 from slipping. In one embodiment of the present invention, a base receptacle, as shown in FIG. 1, with a circular grooved interior surface 10, wherein the depicted circular grooves represent one embodiment of a receiver engagement feature 12, and a plug 7, as shown in FIG. 2, with a circular ribbed exterior surface 14, wherein the depicted circular ribs represent one embodiment of a plug engagement feature 16, will mate together holding the suture leads 18 in place between the interior surface 10 and exterior surface 14, respectively, of the base receptacle 5 and the plug 7. The plug 7 is pressed into engagement with a receiver seat 3 within the through channel 1 through the base receptacle 5 using a tool that may be selected from a securement instrument 21 as shown in FIGS. 4-7, allowing the base receptacle 5 to expand around the plug 7, each of the complimentary engagement features 12, 16 interacting to cause the plug 7 to lock in place within the base receptacle 5, keeping the suture leads 18 secure and keeping the plug 7 from backing out of the base receptacle 5.

Figure 8:
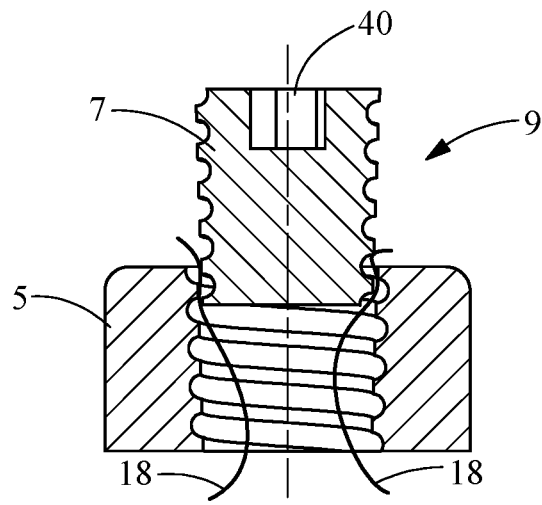
FIG. 8 shows an assembly of the tapered ribbed helical plug and the receptacle with tapered helical surface.
Figure 9:
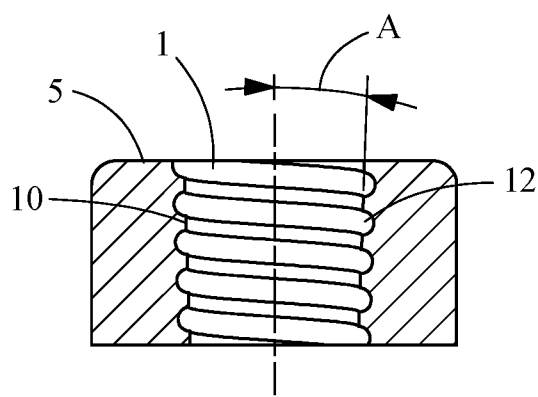
FIG. 9 shows a base receptacle with a tapered helical interior surface.
Figure 10:
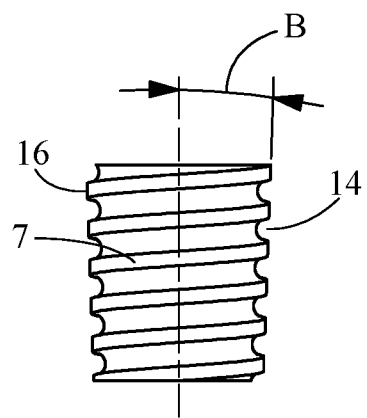
FIG. 10 shows a plug with a tapered helical interior surface.

In another embodiment of the present invention, a base receptacle 5 as shown in FIG. 9 with a helical ribbed interior surface 10 and a plug 7 as shown in FIG. 10 with a helical ribbed exterior surface 14 will mate together holding the suture leads 18 in place between the interior surface 10 and exterior surface 14, respectively, of the base receptacle 5 and the plug 7. The plug 7 is screwed in the base receptacle 5 using a driving feature 40 on the plug 7 as shown in FIG. 10, whereby the helical threads of the receiver engagement feature 12 expand around the threads of the plug engagement feature 16, whereby the plug 7 is locked in place to secure the suture leads 18 and preventing the plug 7 from backing out of the base receptacle 5. It will be appreciated that in the various embodiments, the receiver engagement feature 12 may include structures such as male or female threading that is complimentary to the plug engagement feature 16, as shown in FIG. 8-10, or the receiver engagement feature 12 may include structures such as ridges or channels or grooves that are complimentary with the plug engagement feature 16, as shown in FIG. 1-3. And in some embodiments, the respective receiver and plug engagement features 12, 16 may comprise a Morse taper type engagement (not shown). Thus, as shown in FIG. 1-3 of the drawings, in one embodiment the receiver engagement feature 12 includes female groves that are complimentary to male ribs that form the plug engagement feature 16 on the exterior surface 14 of the plug 7. And, in another embodiment, as shown in FIG. 8-10 of the drawings, the receiver engagement feature 12 includes female threading that is complimentary to male threading that forms the plug engagement feature 16 on the exterior surface 14 of the plug 7.

In accordance with the various embodiments of the suture clamp assembly 9, each of the base receptacle 5 and plug 7 are configured with complimentary tapered profiles, such that the tapered plug 7 fits within a complementary tapered receiver seat within the base receptacle 5. It will be appreciated that in other embodiments, each of the base receptacle 5 and plug 7 may be configured with complimentary profiles that are not tapered, and that may be cylindrical, or include both cylindrical and frustoconical or tapered portions.

In the various embodiments, the base receptacle 5 includes at its upper end 4 a through channel 1 opening into the receiver seat 3 and includes a lower end 6, the through channel 1 being adapted for passage of suture leads form between the upper end 4 out the lower end 6, the receiver seat 3 being adapted to receive and retain the plug 7 within the base receptacle 5 without passage beyond the lower end 6. In some embodiments, the receiver seat 3 is a continuous channel through the base receptacle 5, as shown in the drawings, and in some embodiments the receiver seat 3 is sized to retain the plug 7 and narrows and is sized for permitting passage of sutures through the base receptacle from between the lower end 6 through the upper end 4, but otherwise prevents the further passage of the plug 7 beyond the receiver seat 3.

In accordance with the various embodiments, the receiver seat 3 of the base receptacle 5 includes at one or both of upper and lower ends 4, 6 an edge that is characterized by scalloped or other circumferential recesses for sutures passed through the base receptacle to prevent compression and possible damage when the suture clamp assembly 9 is contacted with bone during tensioning.

In accordance with some embodiments, the suture clamp assembly 9 components are made of implant grade plastic such as PEEK or PMMA. Selection of this material provides a generally lightweight device that may be employed to secure the sutures without insertion into bone. Of course, other materials may be employed, such as other implant grade polymers, carbon fibers, ceramics, metals, and combinations of these. In accordance with some uses of the suture clamp assembly 9, it is desirable for the material to be radiolucent thus only those materials that are radiolucent will be selected. In some embodiments, a radiopaque material may be beneficial to ensure the ability to locate by x-ray after the surgical site is closed. Of course, in some embodiments, a radiolucent material may include radiopaque markers/visual indicia, for example, using tantalum or other material.

The present invention also includes a securement instrument as shown in FIGS. 4-7 that allows multiple suture leads 18 to be tensioned and then locked simultaneously, for example by securement with a suture clamp assembly 9. The mechanisms that allow the insertion of the suture clamp assembly 9, tensioning of the suture leads, and final locking are all incorporated into a single instrument. The instrument includes the following features: a mounting tip 34; a trigger 22; a handle 20 with rack 36; a carriage assembly 23 that includes a pinion knob 30, tension ring 28, and ratchet 38; and an upper slide 24.

In accordance with a representative surgical method according to the disclosure, the inventive system is employed to secure several suture leads without or substantially without the use of knots and with a minimal number of bone anchors.

Figure 11:
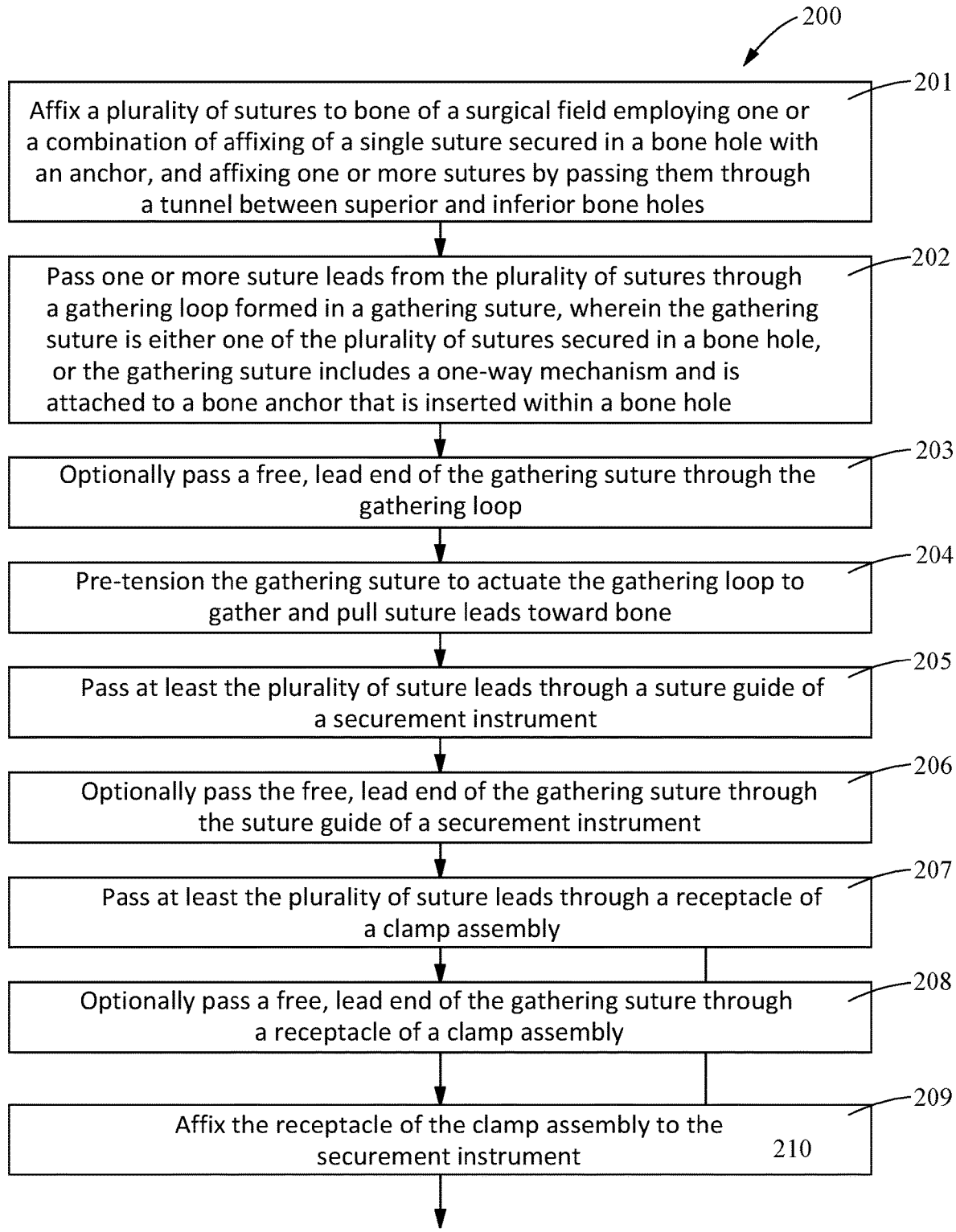
FIG. 11 shows a flow chart of an embodiment of a surgical procedure, according to the disclosure.
Figure 11:
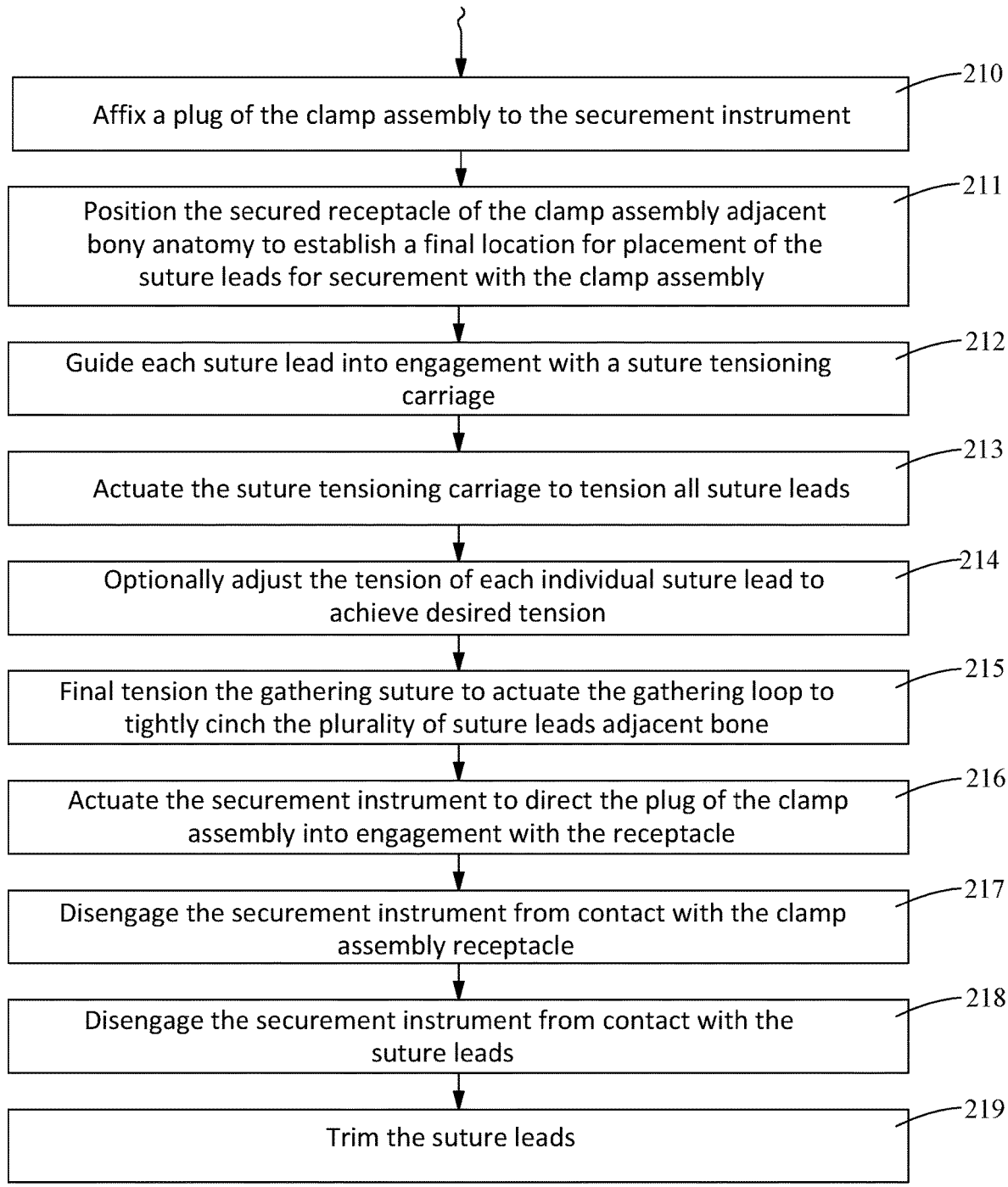
Figure 17:
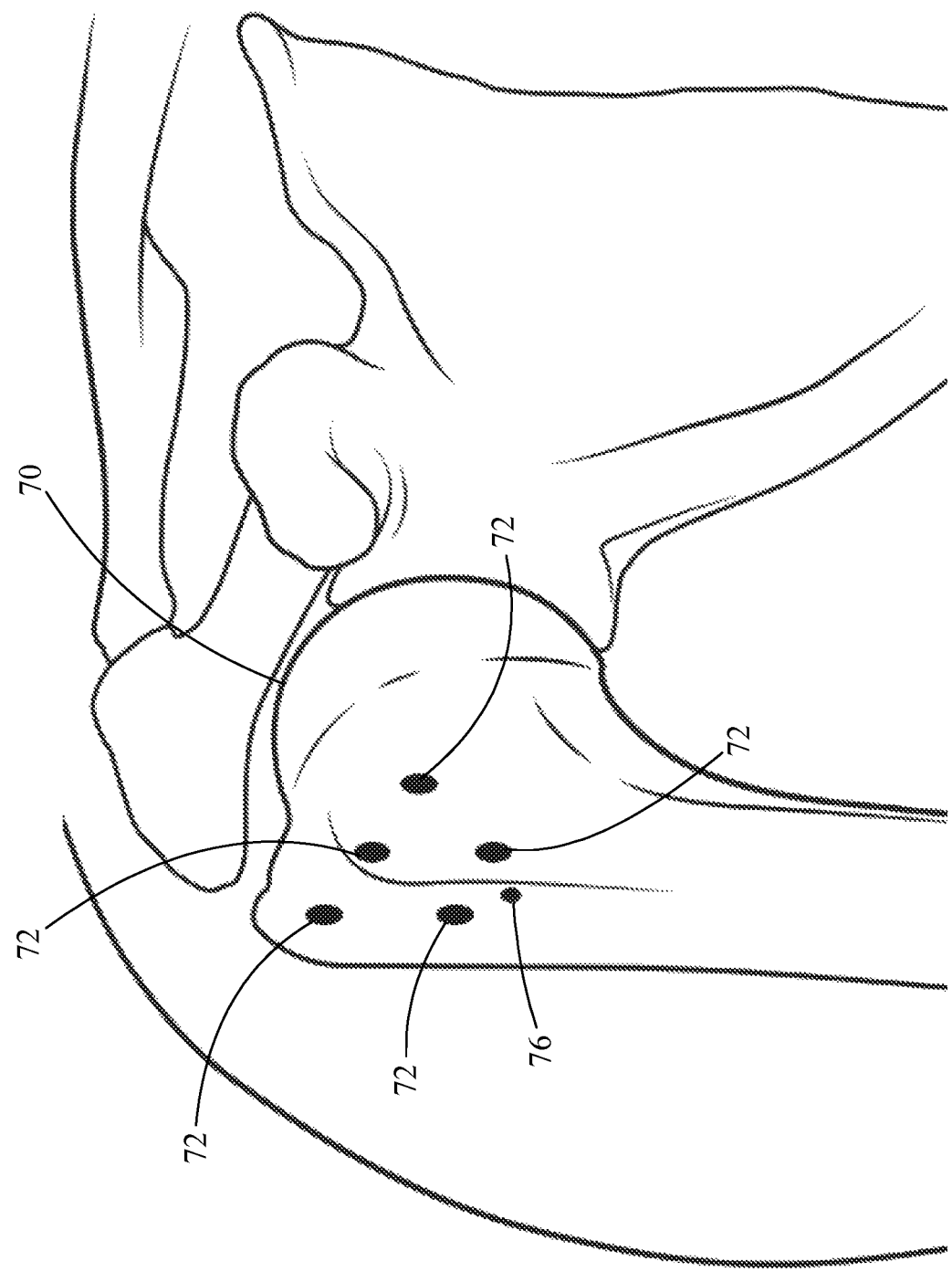
FIG. 17 shows an example of anatomy to which a plurality of sutures may be employed for fixation of soft tissue to bone using the instruments and systems according to the disclosure.
Figure 18:
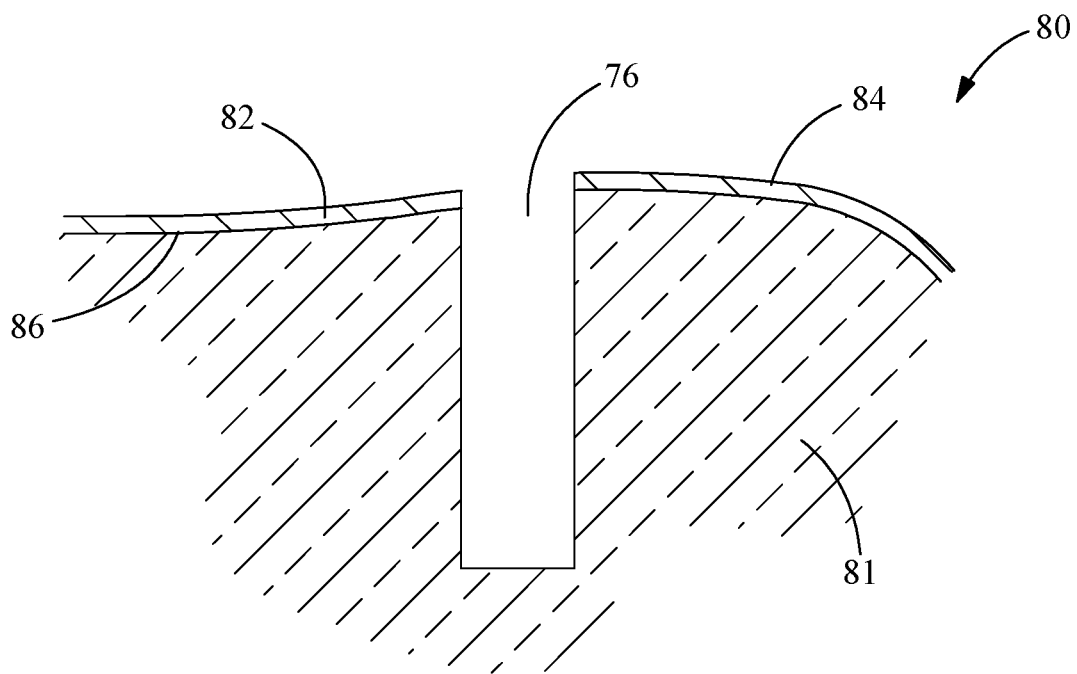
FIG. 18 shows a close-up view of a bone hole as shown in FIG. 17.
Figure 19:
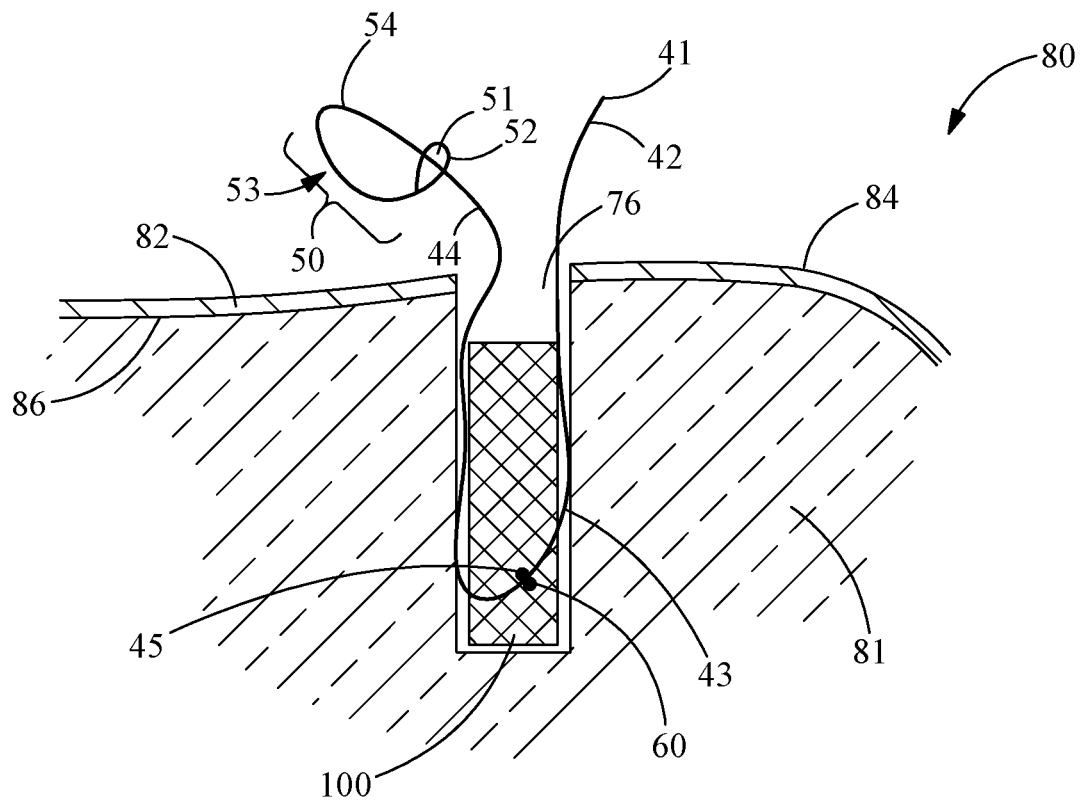
FIG. 19 shows a first view in a sequence illustrating use of a bone anchor to be secured in a bone hole for securing one or a plurality of sutures using the instruments and systems according to the disclosure.
Figure 20:
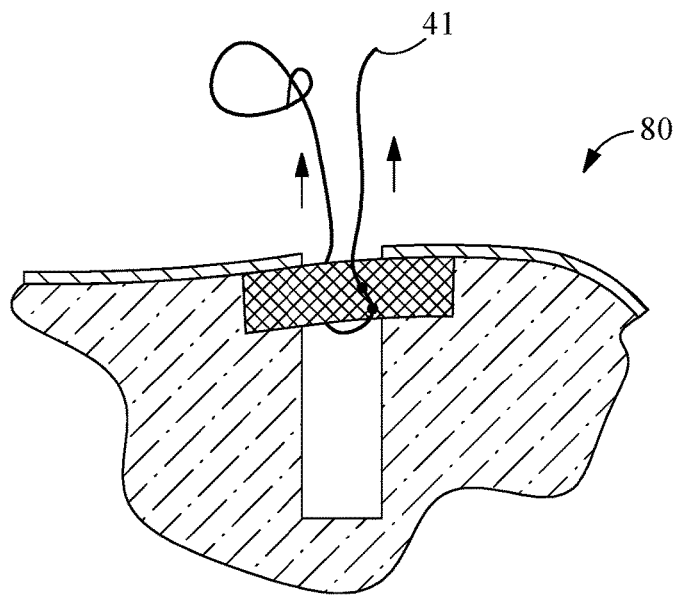
FIG. 20 shows a further view in a sequence as described in relation to FIG. 19.
Figure 21:
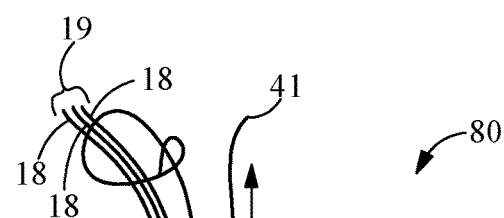
FIG. 21 shows a first view in a sequence as described in relation to FIG. 19.
Figure 22:
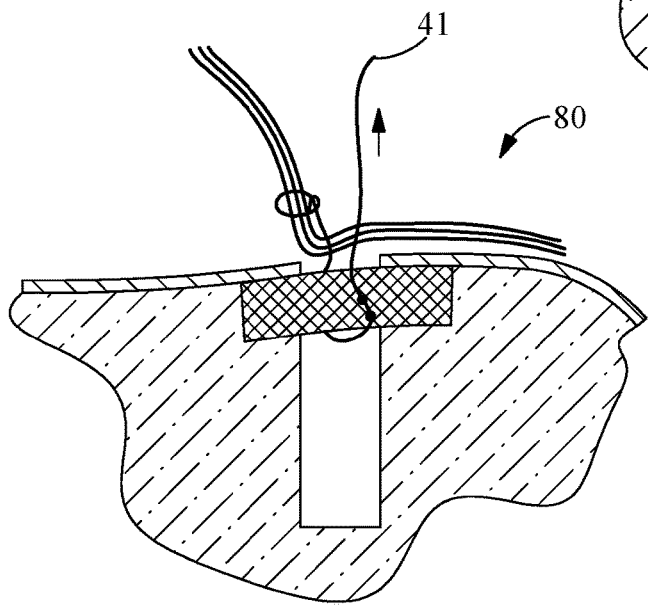
FIG. 22 shows a first view in a sequence as described in relation to FIG. 19.
Figure 23:
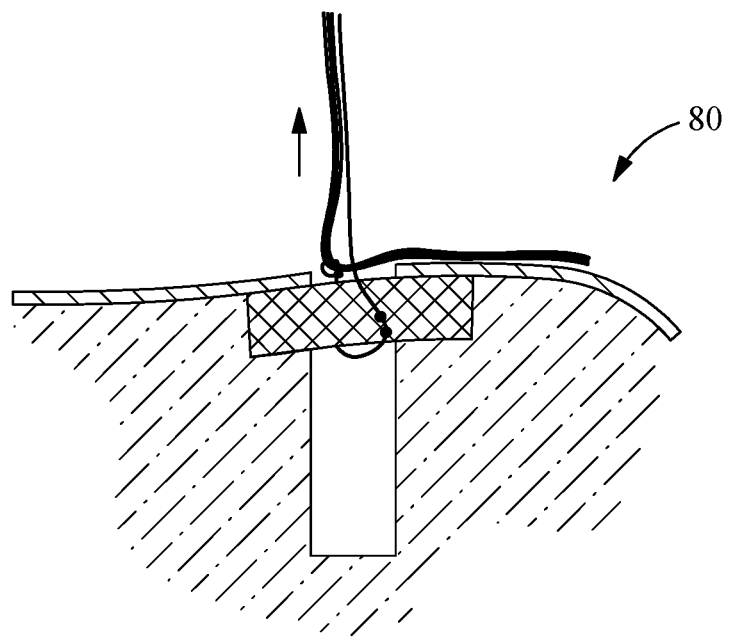
FIG. 23 shows a first view in a sequence as described in relation to FIG. 19.
Figure 24:
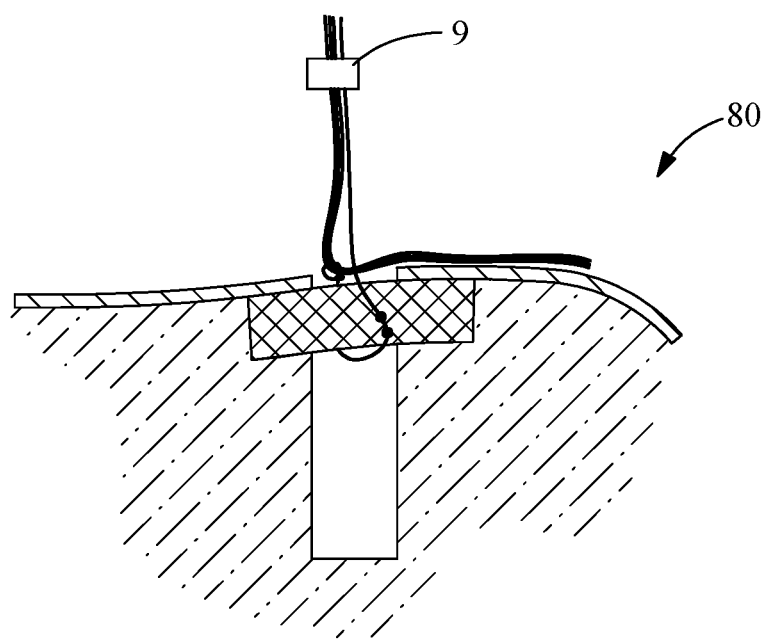
FIG. 24 shows a first view in a sequence as described in relation to FIG. 19.
Figure 25:
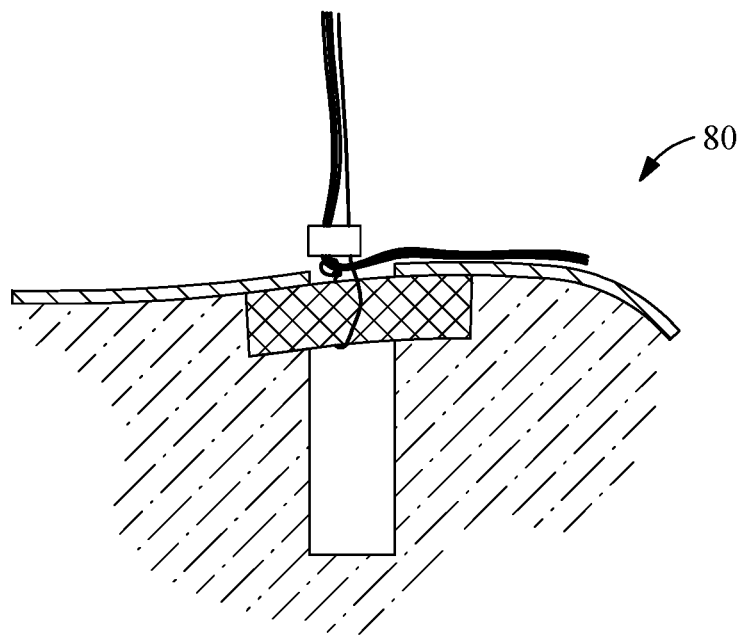
FIG. 25 shows a first view in a sequence as described in relation to FIG. 19.
Figure 26:
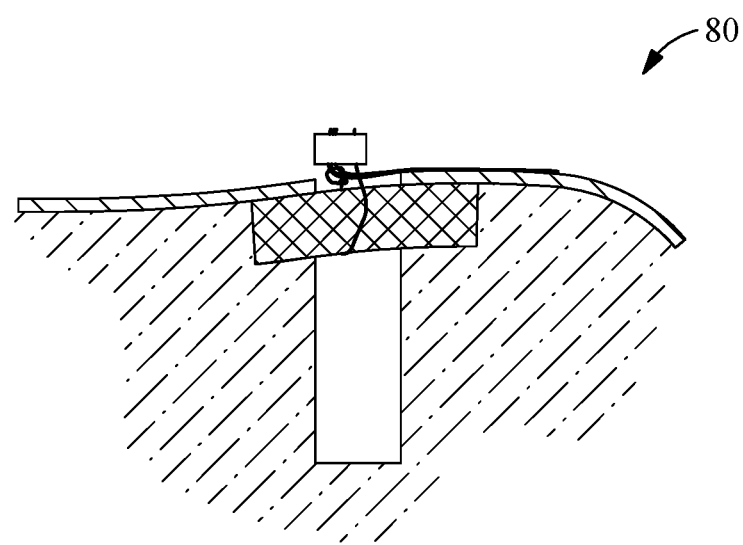
FIG. 26 shows a first view in a sequence as described in relation to FIG. 19.

Referring now to FIG. 11, according to the method, a plurality of sutures are employed to repair and adjust the anatomical placement of soft tissue, for example rotator cuff soft tissue, each suture being secured in or through bone. Thus, each of the plurality of sutures may be affixed to the bone, for example in an arraignment as shown in FIG. 17, wherein each suture may be affixed at one end to an anchor that is secured in bone leaving a free end or lead, or may be passed through a bone channel or tunnel that connects holes that penetrate through the cortical bone and into the cancellous bone, leaving two free leads, one at each bone hole. Further according to the method, all or a subset of each suture lead is captured within a gathering loop of a gathering suture, and after use of the securement instrument, the gathered suture leads are tensioned and then cinched against the bone and secured in place with a clamp assembly. In some examples all of the free suture leads may be gathered and captured in a single gathering loop and then secured with a single clamp assembly. And in yet other examples, two or more subsets of free suture leads may be gathered and captured in a single gathering loop and then secured with a single clamp assembly. In some examples, the gathering suture is one of the plurality of sutures secured to bone. In some other examples, the gathering suture includes a one-way mechanism and is attached to a bone anchor that is inserted within a bone hole. The gathering suture includes a lead end which is actuated by pulling to apply tension that draws the suture leads that are gathered in the loop into contact with bone for cinching. In some examples the lead end of the gathering suture may be passed through the loop and cinched.

It will be appreciated that a variety of the steps according to the method as diagramed in FIG. 11 may be carried out in any order. Thus, according to FIG. 11, the following steps may be varied as described below. It will be understood that the method comprises the following steps, including or excluding the indicate optional steps, and there may be yet other steps that could be employed, for example manual adjustments of suture lead tensioning, crossing of sutures between holes prior to gathering and securing, and the like.

As one initial step, affix a plurality of sutures to bone of a surgical field employing one or a combination of affixing of a single suture secured in a bone hole with an anchor, and affixing one or more sutures by passing them through a tunnel between superior and inferior bone holes.

Provide a gathering suture.

Pass one or more suture leads from the plurality of sutures through a gathering loop formed in the gathering suture. The gathering suture is either one of the plurality of sutures secured in a bone hole, or the gathering suture includes a one-way mechanism and is attached to a bone anchor that is inserted within a bone hole.

Optionally pass a free, lead end of the gathering suture through the gathering loop, which can be done at any time, either with the other suture leads or just prior to final cinching of the gathering loop.

Optionally manually adjust the tension of each individual suture lead to achieve desired tension.

The following steps may be executed in any order:

Pre-tension the gathering suture to actuate the gathering loop to gather and pull suture leads toward bone.

Pass at least the plurality of suture leads through a suture guide of a securement instrument.

Optionally pass the free, lead end of the gathering suture through the suture guide of a securement instrument.

Pass at least the plurality of suture leads through a receptacle of a clamp assembly.

Optionally pass a free, lead end of the gathering suture through a receptacle of a clamp assembly.

Optionally manually adjust the tension of each individual suture lead to achieve desired tension.

The following steps may be executed in any order:

Affix the receptacle of the clamp assembly to the securement instrument.

Affix a plug of the clamp assembly to the securement instrument.

The following steps may be executed in any order:

Position the secured receptacle of the clamp assembly adjacent bony anatomy to establish a final location for placement of the suture leads for securement with the clamp assembly.

Guide each suture lead into engagement with a suture tensioning carriage.

Then:

The following steps may be executed in any order:

Actuate the suture tensioning carriage to tension all suture leads.

Optionally manually adjust the tension of each individual suture lead to achieve desired tension.

Then:

Optionally manually adjust the tension of each individual suture lead to achieve desired tension.

Final tension the gathering suture to actuate the gathering loop to tightly cinch the plurality of suture leads adjacent bone.

Actuate the securement instrument to direct the plug of the clamp assembly into engagement with the receptacle.

The following steps may be executed in any order:

Disengage the securement instrument from contact with the clamp assembly receptacle.

Disengage the securement instrument from contact with the suture leads.

Trim the suture leads.

More specific description of each of the steps that are shown in FIG. 11 is provided herein below with specific reference to the drawings.

Figure 12:
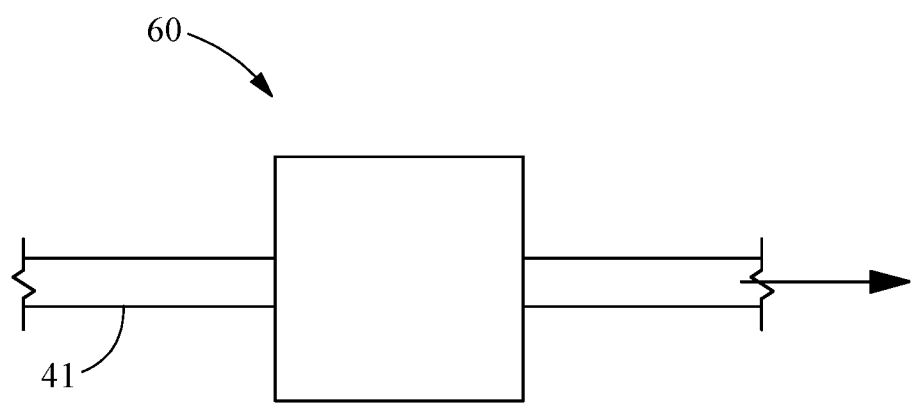
FIG. 12 represents a one-way mechanism that allows the suture to be pulled through in one direction and resist forces pulling back in the other direction.

Referring again to the drawings, FIG. 12 represents a one-way mechanism 60 that will allow a gathering suture 54 to be pulled in one direction and resist pulling in the other. An example of a one way mechanism 60 includes, but is not limited to, a knot tied in a way to allow the suture to be pulled in one direction freely, such as slip knot, and the same knot would tighten around the suture not letting it slip in the other direction. Other suitable examples of a one-way mechanism 60 includes a structure that receives the sutures which includes a mechanical spring, pall or a grip arm that would press against and grip the suture when pulled in one direction and allow it to move freely in the other direction.

Figure 13:
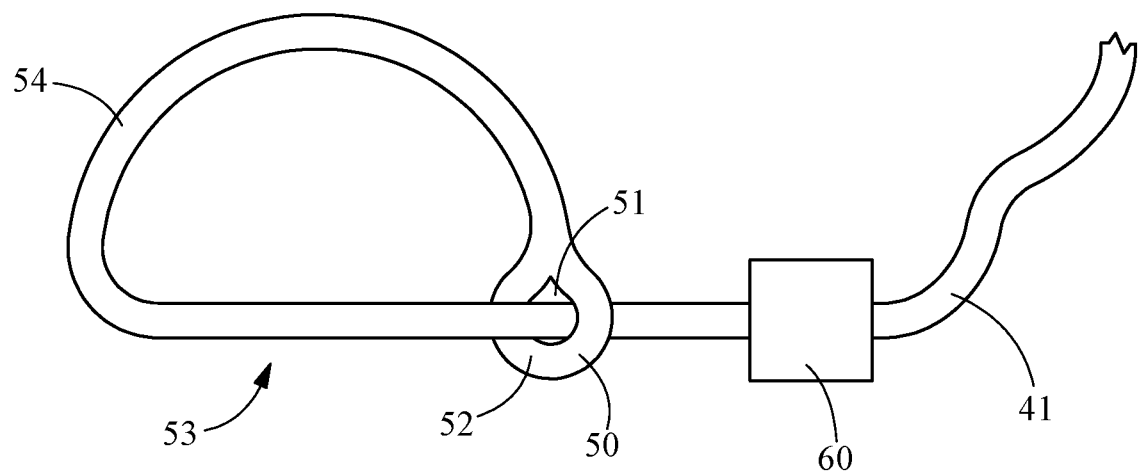
FIG. 13 shows a gathering suture configured with the free end passed through an eyelet and then passed through the one-way mechanism.
Figure 14:
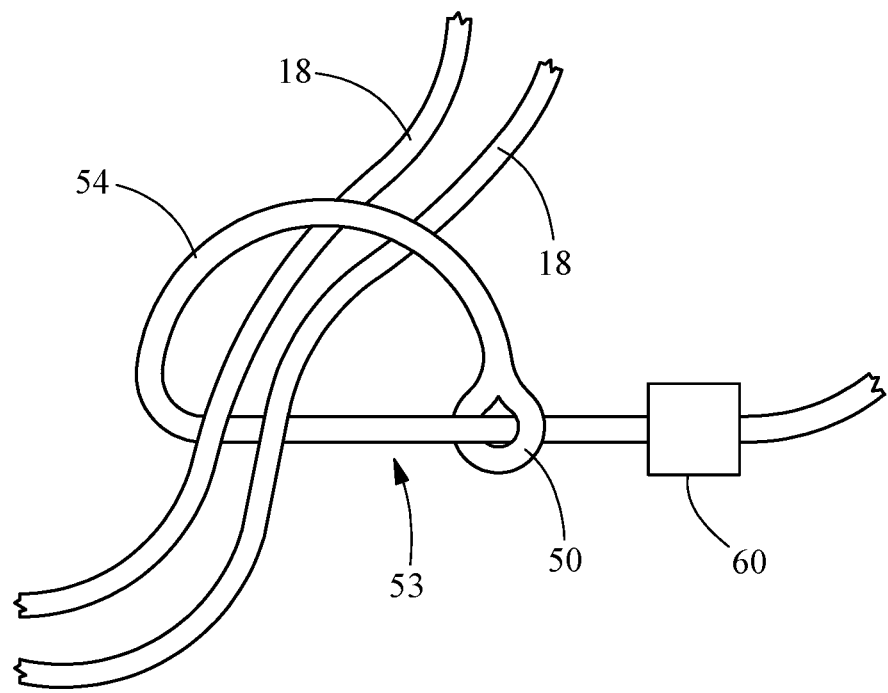
FIG. 14 shows two suture leads passed through the noose opening and the free end passed through the one-way mechanism.
Figure 15:
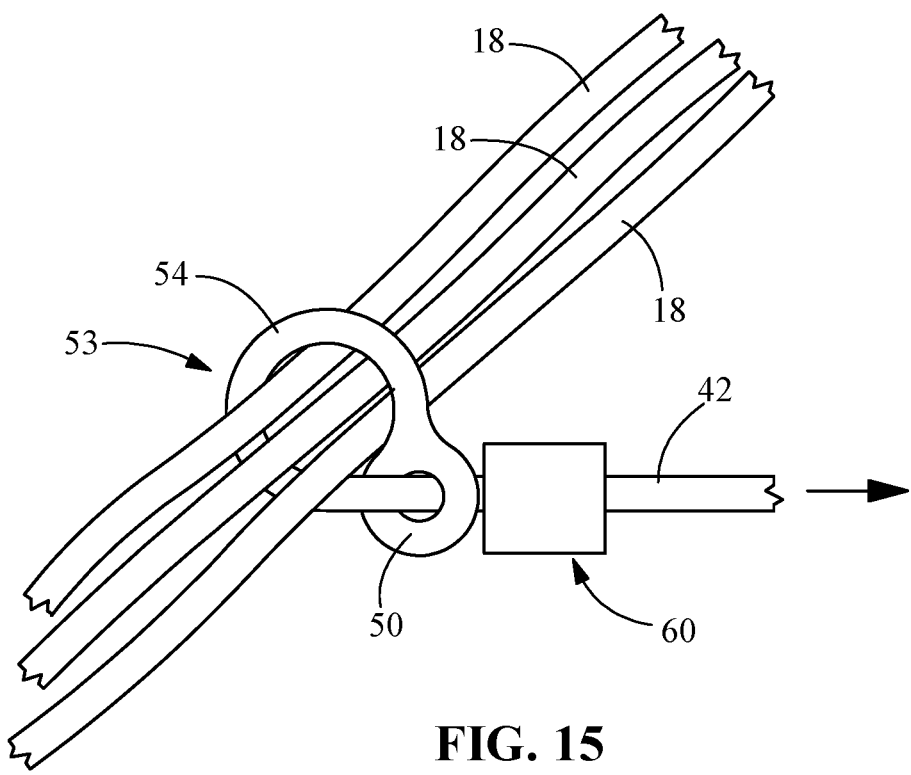
FIG. 15 shows a eyelet of the gathering loop pulled tight against the one-way mechanism, closing the gathering loop around the suture leads creating tension on the suture leads to allow adjustment prior to placing the base receptacle.
Figure 16:
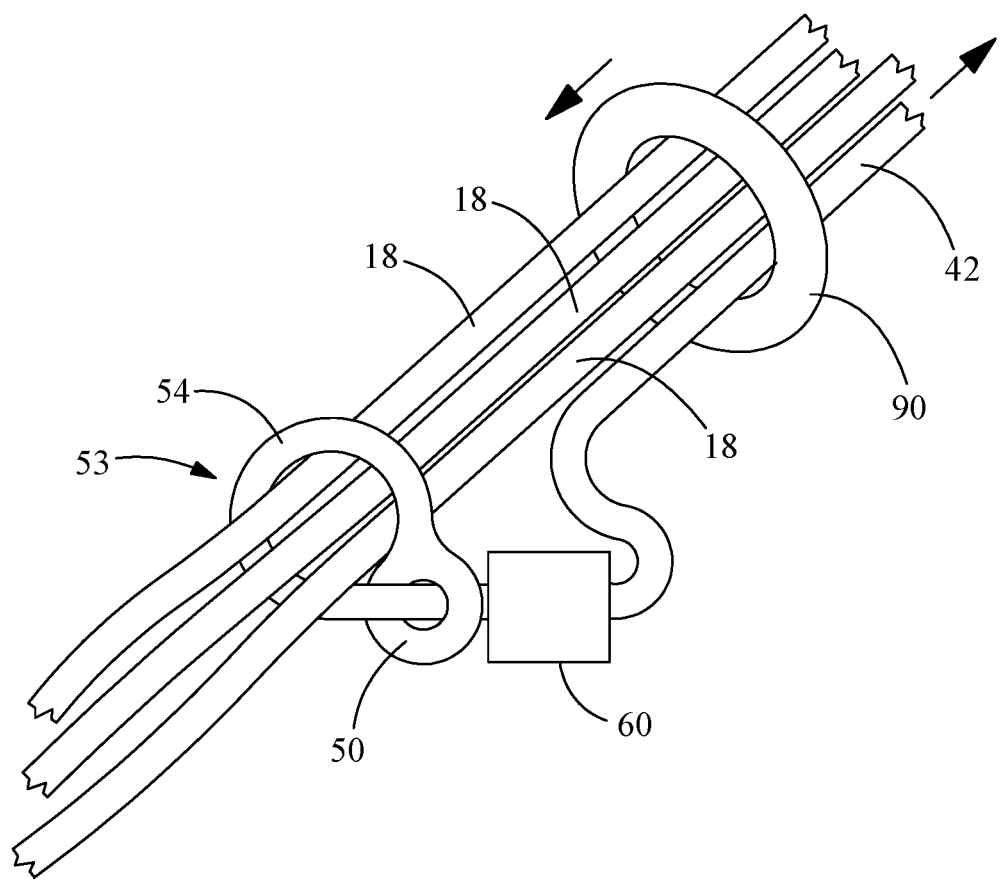
FIG. 16 shows a free end of the gathering loop along with the other suture leads, being passed through the bottom of the base receptacle, the base receptacle being positioned in a direction along the suture leads down to the bone contact point, where the suture leads are tensioned before being secured.

Referring again to the drawings, FIG. 13 shows a gathering loop 53 formed to capture and secure one or a plurality of suture leads 18, the gathering loop 53 including a loop portion 54 of the gathering suture 41, a gathering suture lead 42 (which is a loose end of the gathering suture 41), a loop portion 54 of the gathering suture 41, an eyelet portion 50 that includes an eyelet portion 52 and an eyelet aperture 51. The gathering loop 53 is created by passing the suture lead 42 of the gathering suture 41 through the eyelet 50. The gathering loop 53 forms a noose, lasso, snare or other similar fiber gathering structure capable of gathering together bundles of sutures, such as one or more of suture leads 18. FIG. 14 shows suture leads 18 being passed through the gathering loop 53. FIG. 15 shows a lead 42 of a gathering suture 51 being pretensioned making the eyelet 50 contact the one-way mechanism 60 (for example a knot or other structure as described herein). This will cause the gathering loop 53 to close around the suture leads 18. Tension on each of the individual suture leads 18 and gathering suture lead 41 can be adjusted as needed. FIG. 16 shows suture leads 18, 41 being passed through a generic ring shaped representation of a suture clamp 90 (which may be a suture clamp assembly 9 as shown in FIG. 1-3, for example). FIG. 18-FIG. 26 show a close up view of a bone hole as shown in FIG. 17, and include successive views in a sequence illustrating use of a bone anchor 100 (generically represented as a rectangle, which may be selected from a variety of known anchors as designed herein) to be secured in a bone hole 76 for securing one or a plurality of sutures 18 using the instruments and systems according to the disclosure; wherein a method of securement as described above and shown in FIG. 12-16, further includes the use of a suture anchor 100 that is secured to a gathering suture 41, to provide enhanced securement to bone prior to application of a clamp assembly 90 (represented as a generic clamp having a general rectangular shape in the series of drawings represented by FIGS. 18-26, and as a ring in the series of drawings represented by FIG. 12-16).

In a surgical technique using the inventive clamp and securement instrument, for example as shown in FIG. 11, one or a plurality of suture leads 18 secured to or passed through a tunnel in bone tissue, for example, in the shoulder, as represented in FIG. 17, which shows examples of bone holes 72, 76. The sutures are then passed through soft tissue to be repaired and/or secured, and are then gathered for tensioning and securement by fixation using one or a combination of bone anchors and clamp assembly 9 devices according to the disclosure. The clamp and anchor devices are used in place of all, or substantially all, knots that would otherwise be employed to fix the tension and secure suture leads.

In use, the securing instrument 21 is employed to tension the plurality of suture leads 18 and to affix and secure the clamp assembly 9 to the plurality of suture leads 18. Thus, once the suture leads have been gathered and initially drawn towards bone by pre-tensioning of the gathering suture 41, the plurality of sutures 18 and a suture clamp assembly 9 base receptacle 5 according to the disclosure is secured on the mounting tip 34 at the distal end of the securement instrument 30, and the suture leads 18 are passed through the clamp assembly 9 and loosely passed through slots 29 on the tension ring 28 of the carriage assembly 23. The mounting tip 34 is seated against the bone tissue putting the clamp at its desired final position. The carriage assembly 23 can then be moved to apply tension to the suture leads 18. To move the carriage assembly 23, the pinion knob 30 is rotated. This causes the carriage assembly 23 to move along the rack 36 in a proximal direct towards the rear handle 20 (and towards the user of the securement instrument 21) along the long axis of the securement instrument 21 as shown in FIG. 7. This pinion knob 30 includes tension dial which provide an indicator of the force applied to move the carriage assembly 23 to the next notch on the rack 36. The ratchet 38 is what holds the carriage assembly 23 in place and keeps the tension on the suture leads 18 so they can be locked. To lock the suture leads, the trigger 22 is pulled toward the rear handle 20. This causes the upper slide 24 to move towards the distal end of the instrument. The plug inserter 26 which is at the distal end of the securement instrument 21 and opposes the mounting tip 34, and is situated to engage a driving feature 40 of the plug 7 and travel along the long axis of the securement instrument 21 to introduce the plug 7 into the through channel 1 of the base receptacle 5. Accordingly, actuation of the upper slide 24 drives the slide distally along the securement instrument long axis and applies force to the proximal end 12 of the plug 7, passing the plug 7 into the through channel 2 and causing the exterior surface 14 of the plug 7 into contact with the interior surface 10 of the base receptacle 5 to seat the plug 7 in the receiver seat 3 and engage the base receptacle 5 and plug 7 complimentary engagement features 14, 16, thereby pressing the suture leads 18 and locking them in place in compression between the plug 7 and the base receptacle 5. The securement instrument 21 is used to carry out several of the steps of the exemplary method shown in FIG. 11, and to thereby provide final securement of suture leads without the need for many or even any hand tied knots.

Referring again to the drawings, FIG. 27-FIG. 30 show in the context of shoulder anatomy that includes a humerus examples of possible final securement configurations of sutures employing the system, devices and methods of the invention.

Figure 27:
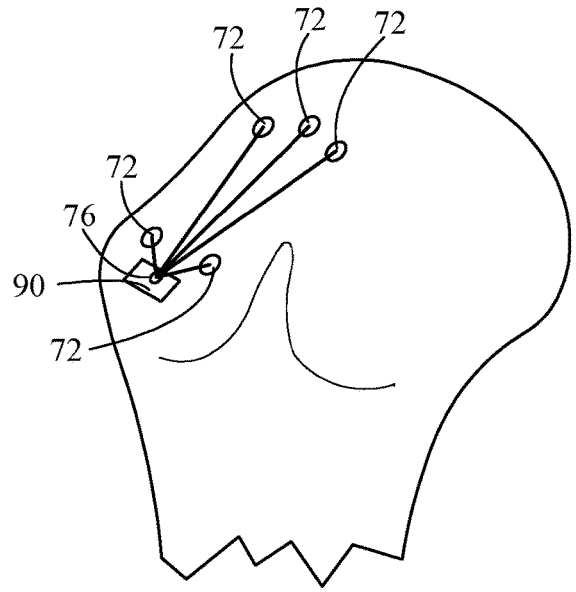
FIG. 27 shows a view of the anatomy as described in relation to FIG. 17 to which a plurality of sutures has been secured to bone via a bone hole and a bone anchor using the instruments and systems according to the disclosure.

FIG. 27 shows a plurality of anchored sutures with no bone tunnels wherein the leads are all gathered with a loop of a gathering suture and secured to a central anchor within bone hole and then locked into tension with a generically represented clamp assembly 90.

Figure 28:
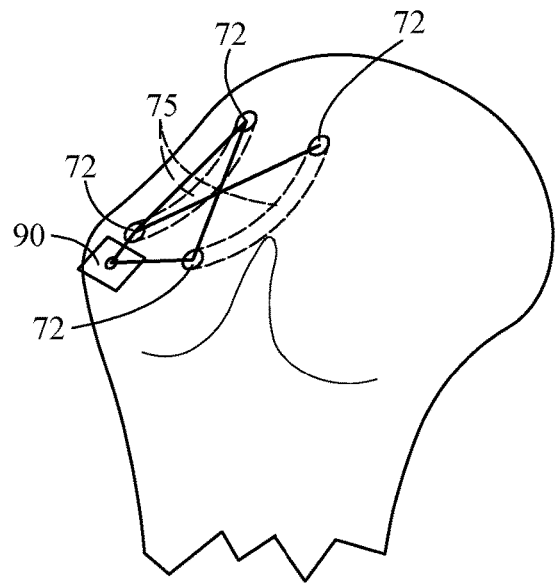
FIG. 28 shows an alternate view of anatomy to which a plurality of sutures may be employed for fixation of soft tissue to bone using the instruments and systems according to the disclosure, wherein sutures are passed into one hole and out another via a tunnel from cortical through cancellous bone and out through cortical bone employing a bone anchor.

FIG. 28 shows a plurality of anchored sutures through bone tunnels wherein the leads are all gathered with a loop of a gathering suture and secured to a laterally positioned anchor within a bone hole and then locked into tension with a generically represented clamp assembly 90.

Figure 29:
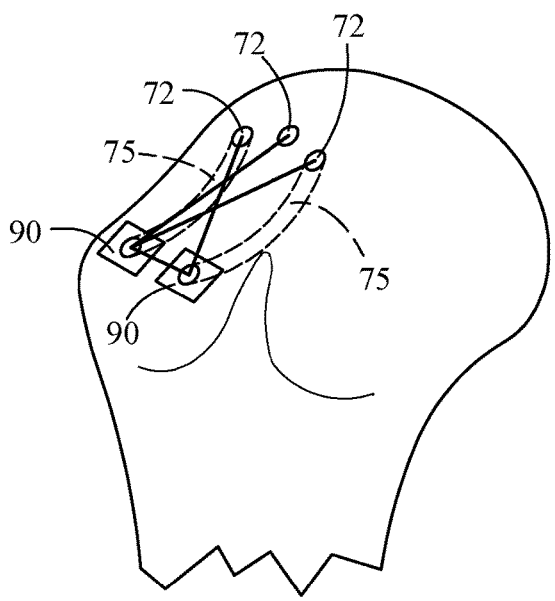
FIG. 29 shows an alternate view of anatomy to which a plurality of sutures may be employed for fixation of soft tissue to bone using the instruments and systems according to the disclosure, wherein sutures are passed into one hole and out another via a tunnel from cortical through cancellous bone and out through cortical bone (without employing bone anchors)

FIG. 29 shows a plurality of anchored sutures through bone tunnels and a single anchored suture coming from the center top wherein the leads are split into two sub groups, and each group is all gathered with a loop of a gathering suture and locked into tension with a generically represented clamp assembly 90.

Figure 30:
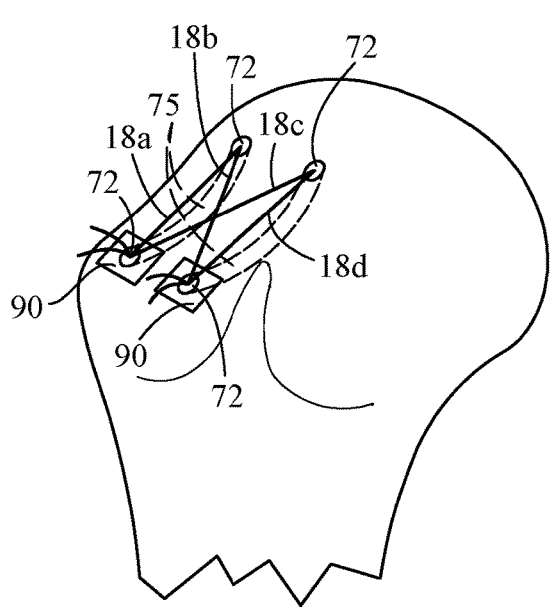
FIG. 30 shows a view of the anatomy as described in relation to FIG. 28 to which a plurality of sutures has been secured adjacent to bone using the instruments and systems according to the disclosure.

FIG. 30 shows a plurality of anchored sutures that include two sutures through each of two bone tunnels wherein the leads are split into two sub groups, and each group is all gathered with a loop of a gathering suture and locked into tension with a generically represented clamp assembly 90.

It will be appreciated that the logic underlying the arraignment of holes and sutures is that any of a variety of arrangements are possible for use with (1) only a clamp, and for use with (2) a clamp 90 and an anchor 100, where the sutures may be secured either at a lateral anchor hole or at an anchor hole that is not necessarily lateral. It will further be appreciated that according to the disclosure, there are no specific limits or requirements as to the site of tissue in the body wherein the invention may be employed; while the drawings and the description provide the shoulder as an example, other sites such as knees, hips and other large and small bones would benefit from use of the invention. Moreover, the examples and drawings do not in any manner limit the number, placement, size, and arrangement of bone holes and tunnels that may be employed for securing sutures to bone.

In some embodiments, a suture locking system is provided, comprising: an implantable clamp assembly comprising a base receptacle and a plug insertable within the base receptacle, each of the receptacle and plug having complimentary surfaces that interfit to secure the plug within the base receptacle, the contact surfaces when interfitted providing an interface suitable for securing one or more sutures passed there between; and a securement instrument having distal and proximal ends that is engageable with the base receptacle of the clamp assembly, at least one suture comprising a gathering loop, and one or more sutures, the securement instrument comprising: a distal holding end; a trigger; a rear handle that comprises a rack; a carriage assembly that comprises a pinion knob; a suture tension ring, and a ratchet; and an upper slide; wherein the securement instrument, in use, is secured to the base receptacle secured at the distal end of the instrument, and at least one suture is passed through the clamp assembly and loosely passed through tension ring of the carriage, the distal end of the instrument is seated against tissue, the carriage assembly is moved to apply tension to the at least one suture, the pinion knob is rotated along the rack to move the carriage assembly to move towards the rear handle according to a force that is selected on the pinion knob, the ratchet holding the carriage assembly in place and the at least one suture in tension, and wherein actuation of the trigger toward the rear handle causes the upper slide to move towards the distal end of the instrument to apply force to the top of the plug provisionally placed at the upper end of the base receptacle, the force causing the plug to pass into the receiving seat, compressing the at least one suture lead into place to lock the sutures and clamp assembly.

In some embodiments, a suture locking system includes a gathering suture formed into a gathering loop to gather the one or more sutures passed through the through channel. In some embodiments, the gathering loop includes an eyelet through which the gathering suture passes to draw the sutures passed through the through channel together. In some embodiments, a suture locking system includes a one-way device arranged and disposed to tension the gathering suture in a single direction. In some embodiments, a suture locking system includes receptacle comprises upper and lower ends, an exterior surface and a through channel from the upper and lower ends, the through channel including a receiver seat. In some embodiments, each of the base receptacle and the tapered plug include complementary receiver seat and plug engagement features to retain the tapered plug within the tapered receiver seat and to retain one or more sutures passed through the through channel by compression thereof between the complementary receiver seat and plug engagement features. In some embodiments, a suture locking system includes comprising a one-way device arranged and disposed to tension the gathering suture in a single direction. In some embodiments one or both of the base receptacle and the tapered plug of the implantable clamp assembly is formed from a radiolucent plastic. In some embodiments each of the tapered receiver seat and the tapered plug includes a taper that is angled between 0.5 and 10 degrees. In some embodiments the base receptacle includes at its upper end an opening into the receiver seat and includes at a lower end a suture passage, the receiver seat being adapted to receive and retain the plug within the base receptacle without passage beyond the lower end. In some embodiments the receiver seat is a continuous channel through the base receptacle, and the receiver seat is sized to retain the plug and narrows to a distal suture channel that is sized for receiving sutures passed through the base receptacle from the lower end through the upper end, but otherwise prevents the further passage of the plug beyond the receiver seat. In some embodiments the complimentary mating surfaces of the base receptacle and the tapered plug may be selected from a series of circumferential grooves on the receptacle and ribs on the plug, and spiral grooves on the receptacle and threads on the plug. In some embodiments the base receptacle and the tapered plug inter-engage by snap fitting or threaded engagement between the complimentary surfaces. In some embodiments the complimentary surfaces of the base receptacle and the tapered plug generally lack sharp edges and angles to prevent cutting the sutures passed therethrough and are adapted with sufficient clearance to prevent binding and shearing of the sutures. In some embodiments the receiver seat of the base receptacle includes at one or both of upper and lower ends an edge that is characterized by scalloped or other circumferential recesses for sutures passed through the base receptacle to prevent compression and possible damage when the clamp assembly is contacted with bone during tensioning.

In some embodiments, a locking system is provided, comprising: an implantable clamp assembly comprising: a base receptacle comprising upper and lower ends, an exterior surface and a through channel from the upper and lower ends, the through channel including a tapered receiver seat; and a tapered plug; wherein each of the base receptacle and the tapered plug include complementary receiver seat and plug engagement features to retain the tapered plug within the tapered receiver seat and to retain one or more sutures passed through the through channel by compression thereof between the complementary receiver seat and plug engagement features; and a securement instrument having distal and proximal ends that is engageable with the base receptacle of the clamp assembly and one or more sutures, the securement instrument comprising: a distal holding end; a trigger; a rear handle that comprises a rack; a carriage assembly that comprises a pinion knob; a suture tension ring, and a ratchet; and an upper slide; wherein the securement instrument, in use, is secured to the base receptacle secured at the distal end of the instrument, and at least one suture is passed through the clamp assembly and loosely passed through tension ring of the carriage, the distal end of the instrument is seated against tissue, the carriage assembly is moved to apply tension to the at least one suture, the pinion knob is rotated along the rack to move the carriage assembly to move towards the rear handle according to a force that is selected on the pinion knob, the ratchet holding the carriage assembly in place and the at least one suture in tension, and wherein actuation of the trigger toward the rear handle causes the upper slide to move towards the distal end of the instrument to apply force to the top of the plug provisionally placed at the upper end of the base receptacle, the force causing the plug to pass into the receiving seat, compressing the at least one suture lead into place to lock the sutures and clamp assembly.

In some embodiments, a method for surgically repairing rotator cuff damage, comprising: selecting an implantable clamp assembly comprising: a base receptacle comprising upper and lower ends, an exterior surface and a through channel from the upper and lower ends, the through channel including a tapered receiver seat; and a tapered plug, wherein each of the base receptacle and the tapered plug include complementary receiver seat and plug engagement features to retain the tapered plug within the tapered receiver seat and to retain one or more sutures passed through the through channel by compression thereof between the complementary receiver seat and plug engagement features; collecting suture leads from at least two suture anchors that have been implanted within tissue adjacent shoulder rotator cuff, at least one of the two suture leads originating from a suture anchor on a rotator cuff medial surface and at least one of the two suture leads originating from a suture anchor on a rotator cuff lateral surface, wherein the two or more anchors are characterized as one of hard and soft, and wherein each of the two or more anchors are selected from single lead sutures and double lead sutures; passing the two or more suture leads through the through channel of the clamp assembly; contacting the base receptacle of the claim assembly against a tissue surface and applying tension to the suture leads; assembling the clamp assembly by insertion of the plug into the tapered receiver seat to lock the tensioned sutures within the clamp assembly.

In some embodiments the method further comprises, prior to passing the two or more suture leads through the through channel of the clamp assembly, gathering a group of the suture leads at a fixation point in the bone, the gathering including passing the group of suture leads through a gathering loop formed of a gathering suture and a one-way mechanism arranged and disposed to tension the gathering suture in a single direction. In some embodiments the method further comprises pre-tensioning the gathering loop to pull the leads to the bone surface. In some embodiments the clamp assembly is pre-assembled before passage of the sutures within the through channel.

While various inventive aspects, concepts, and features of the general inventive concepts are described and illustrated herein in the context of various exemplary embodiments, these various aspects, concepts, and features may be used in many alternative embodiments, either individually or in various combinations and sub-combinations thereof. Unless expressly excluded herein, all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts, or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary, or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

What is claimed is:

1. A suture locking system, comprising:
   a) an implantable clamp assembly comprising a base receptacle and a plug insertable within the base receptacle, each of the receptacle and plug having complimentary surfaces that interfit to secure the plug within the base receptacle, the complimentary surfaces, when interfitted, providing an interface suitable for securing one or more sutures passed there between; and
   b) a securement instrument having distal and proximal ends and that is engagable with the base receptacle of the clamp assembly and one or more sutures to direct tensioning and locking of the sutures with the clamp assembly, the securement instrument comprising a mounting tip for retaining and securing the clamp assembly base receptacle and for gathering and securing a one or a plurality of suture, and a plug inserter, the mounting tip and the plug inserter arranged in-line along a long axis of the instrument defined from the distal to proximal end, the instrument further comprising a carriage assembly that comprise a tension ring for securing the plurality of sutures, the carriage assembly adapted to translate between proximal to distal along the instrument's long axis.

2. The suture locking system according to claim 1, the securement instrument further comprising a distal holding end that comprises the mounting tip; a trigger; a handle that comprises a pinion knob, the suture tension ring, a rack, and a ratchet; and an upper slide that comprises at a distal end the plug inserter.

3. The suture locking system according to claim 1, wherein the securement instrument, in use, is secured to the base receptacle secured at the distal end of the instrument, and at least one suture is passed through the clamp assembly and loosely passed through tension ring of the carriage, the distal end of the instrument is seated against tissue, the carriage assembly is moved to apply tension to the at least one suture, the pinion knob is rotated along the rack to move the carriage assembly towards the rear handle according to a force that is selected on the pinion knob, the ratchet holding the carriage assembly in place and the at least one suture in tension, and wherein actuation of the trigger toward the rear handle causes the upper slide to move towards the distal end of the instrument to apply force to the top of the plug provisionally placed at the upper end of the base receptacle, the force causing the plug to pass into the receiving seat, compressing the at least one suture lead into place to lock the sutures and clamp assembly.

4. The suture locking system according to claim 1, further comprising a gathering suture that comprises a free end comprising a lead and a gathering end comprising a gathering loop.

5. The suture locking system according to claim 4, wherein the gathering loop includes an eyelet through which the lead end may be passed to cinch the loop.

6. The suture locking system according to claim 5, further comprising a one-way device arranged and disposed to tension the gathering suture in a single direction, the one way device selected from a slip knot, mechanical spring, pall or grip arm.

7. The suture locking system according to claim 5, wherein each of the base receptacle and the plug include complementary receiver seat and plug engagement features selected from grooves, ribs, and male and female threads to retain the tapered plug within the tapered receiver seat and to retain one or more sutures passed through the through channel by compression thereof between the complementary receiver seat and plug engagement features.

8. The suture locking system according to claim 7, wherein each of the receiver seat and the plug includes a taper that is angled between 0.5 and 10 degrees.

9. The suture locking system according to claim 1, wherein the base receptacle comprises upper and lower ends, an exterior surface and a through channel from the upper and lower ends, the through channel including a receiver seat.

10. The suture locking system according to claim 1, wherein one or both of the base receptacle and the plug of the implantable clamp assembly is formed from a radiolucent plastic.

11. The suture locking system according to claim 9, wherein the receiver seat of the base receptacle includes at one or both of upper and lower ends an edge that is characterized by scalloped or other circumferential recesses for sutures passed through the base receptacle to prevent compression and possible damage when the clamp assembly is contacted with bone during tensioning.

12. A medical device, comprising: a securement instrument for tensioning and locking a plurality of sutures, the securement instrument having distal and proximal ends and is engagable with a base receptacle of a clamp assembly and one or more sutures to direct tensioning and locking of the sutures with the clamp assembly, the securement instrument comprising a mounting tip for retaining and securing the clamp assembly base receptacle and for gathering and securing a one or a plurality of suture, and a plug inserter, the mounting tip and plug inserter arranged in-line along a long axis of the instrument defined from the distal to proximal end, the instrument further comprising a carriage assembly that comprise a tension ring for securing the plurality of sutures, the carriage assembly adapted to translate between proximal to distal along the instrument's long axis.

13. The medical device according to claim 12, the securement instrument further comprising a distal holding end that comprises the mounting tip; a trigger; a handle that comprises a pinion knob, the suture tension ring, a rack, and a ratchet; and an upper slide that comprises at a distal end the plug inserter.

14. The medical device according to claim 12, wherein the securement instrument, in use, is secured to the base receptacle secured at the distal end of the instrument, and at least one suture is passed through the clamp assembly and loosely passed through the tension ring of the carriage, the distal end of the instrument is seated against tissue, the carriage assembly is moved to apply tension to the at least one suture, the pinion knob is rotated along the rack to move the carriage assembly towards the rear handle according to a force that is selected on the pinion knob, the ratchet holding the carriage assembly in place and the at least one suture in tension, and wherein actuation of the trigger toward the rear handle causes the upper slide to move towards the distal end of the instrument to apply force to the top of the plug provisionally placed at the upper end of the base receptacle, the force causing the plug to pass into the receiving seat, compressing the at least one suture lead into place to lock the sutures and clamp assembly.

\* \* \* \* \*